(12) United States Patent
Salazar

(10) Patent No.: US 7,439,349 B2
(45) Date of Patent: Oct. 21, 2008

(54) METHOD FOR PREPARATION OF LARGE VOLUME BATCHES OF POLY-ICLC WITH INCREASED BIOLOGICAL POTENCY; THERAPEUTIC, CLINICAL AND VETERINARY USES THEREOF

(76) Inventor: Andres Salazar, 3203 Cleveland Ave., NW, Washington, DC (US) 20008

( * ) Notice: Subject to any disclaimer, the term of this patent is extended or adjusted under 35 U.S.C. 154(b) by 459 days.

(21) Appl. No.: 10/611,614

(22) Filed: Jul. 1, 2003

(65) Prior Publication Data

US 2004/0005998 A1    Jan. 8, 2004

Related U.S. Application Data

(60) Provisional application No. 60/393,713, filed on Jul. 3, 2002.

(51) Int. Cl.
  *C07H 19/04*  (2006.01)
  *A01N 43/04*  (2006.01)
  *A61K 31/70*  (2006.01)
(52) U.S. Cl. .................. 536/26.1; 514/47; 514/48; 514/49; 514/52
(58) Field of Classification Search ................ None
See application file for complete search history.

(56) References Cited

U.S. PATENT DOCUMENTS 4,349,538 A * 9/1982 Levy .................. 514/44

OTHER PUBLICATIONS

Bever, C., A. Salazar, et al. (1986). "Preliminary trial of poly-ICLC in chronic progressive multiple sclerosis." *Neurology* 36(4): 489-493.
Burgasova, M. (1977). "Study of the antiviral activity of a poly I: Poly-C complex with poly-l-lysine in monkeys." *Antibiotiki* 22(5): 458-60.
Ewel, C., W. Urba, et al. (1992), "Polyinosinic-Polycytidylic acid complexed with poly-L lysine and corboxymethylcellulose in combination with interleukin 2 in patients with cancer: clinical and immunological effects." *Cancer Research* 52: 3005-3010.
Geiss, G., G. Jin, et al. (2001), "A comprehensive view of regulatio of gene expression by double-stranded RNA-mediated cell signaling." *J Biol Chem* 276 (32): 30178-30182.
Harrington, D., D. Hlmas, et al. (1977). "Intranasal infection of monkeys with Japanese encephalitis virus: clinical response and treatment with a nuclease-resistant derivative of poly (I) poly (C)." *Am. J Tropical Med Hygiene* 26(6): 1191-97.
Jacobs, B. and J. Langland (1996). "When two strands are better than one: the mediators and modulators of the cellular responses to double stranded RNA." *Virology* 219: 339-349.
Katze, M. G. (1992). "The war against the interferon-induced dsRNA-activated protein kinase, can viruses win?" *Journal of Interferon Research* 12: 241-248.
Levy, H. and E. Lvovsky (1978). "Topical treatment of vaccinia virus infecton with an interferon inducer in rabbits." *J Infect Dis* 137 (1): 78-81.
Levy, H. and C. Bever (1988). Immune modulating effects of PICLC in mice, monkeys, and man. *Applied Bioactive Polymers*. C. Carraher and V. Foster. New York, Plenum.
Maluish, A., J. Reid, et al. (1985). "Immunomodulatory effect of Poly-ICLC in cancer patients." *J Biol Resp Modif* 4: 656-663.
Marcus, P. and M. Sekellick (2001). "Combined sequential treatment with interferon and dsRNA abrogates virus resistance to interferon action." *J. Interferon Cytokine Res* 21: 423-429.
Salazar, A., H. Levy, et al. (1996). "Long-term IM Poly-ICLC treatment of malignant glioma: an open pilot study." *Neurosurgery* 38(6): 1096-1104.
Salazar, A., J. Morales, et al. (1990). "Intramuscular Poly-IClC in HIV Infection: Preliminary findings." *Neurology* 40 (Suppl 1): 238.
Stephen, E., D. Hilmas, et al. (1977). "Swine influenza virus vaccine: potentiation of antibody responses in rhesus monkeys." *Science* 197: 1289-1290.
Stephen, E., M. Samos, et al. (1977). "Effect of a nuclease resistant derivative of polyriboinosinic-polyribocytidylic acid complex on yellow fever in rhesus monkeys." *J Infect Dis* 136(1): 122-6.
Talmadge, J. and D. Hartman (1985). "Optimization of an immunotherapeutic protocol with Poly-ICLC." *Journal of Biological Response Modifiers* 4: 484-489.
Wong, J., E. Saravolac, et al. (1995). "Porphylactic and therapeutic efficacies of poly (ICLC) against respiratory influenza A virus infection in mice." *Antimicrob Agents Chemother* 39(11): 2574-2576.
Worthington, M. and S. Baron (1973). "Effect of poly IC and antibody on infection of immunosuppressed mice with vaccinia virus." *J Infect Dis* 128(3): 308-11.

* cited by examiner

*Primary Examiner*—Shaojia Anna Jiang
*Assistant Examiner*—Layla Bland
(74) *Attorney, Agent, or Firm*—Max Stul Oppenheimer

(57) ABSTRACT

Method for producing large lots of final sterile Poly-ICLC suitable for clinical use with reduced toxicity at effective dose levels, and method for using Poly-ICLC to regulate genes, and method for using Poly-ICLC to treat certain human and veterinary infectious, neoplastic and autoimmune disorders.

4 Claims, 5 Drawing Sheets

Figure 1. Systemic Response to a Single Intranasal dose of Poly-ICLC in Rhesus Monkeys

| Monkey # | Plasma Interferon titer<br>Baseline (Intl. U) | Plasma Interferon titer<br>24 Hours (Intl. U) |
| --- | --- | --- |
| CE 5 F | <3 | 200 |
| CF 61 | <3 | 200 |
| CF 67 | <3 | 700 |
| CF4J | <3 | 700 |
| CF 8F | <3 | 700 |
| CF 5X | <3 | <3 |
| CF 45 | <3 | 100 |
| CF 4R | <3 | 200 |

Figure 2. Induction of Interferon in Rhesus Monkeys by 2mg/kg IV of Poly-ICLC as described in the present application (lot # RBP 10005) (Compare to table II in Levy'82, patent #4,349,538 treatment with 3mg/kg PICLC)

| Monkey# | Hr. Bleed | IFN U/mL | IFN (Levy'82) |
|---|---|---|---|
| Rh H572 | 0 hr. | 3 | |
| Rh H573 | | <3 | |
| Rh H574 | | <3 | |
| Rh H578 | | <3 | |
| Rh H572 | 8 hr. | 7000 | 125-6000 |
| Rh H573 | | 7000 | |
| Rh H574 | | 7000 | |
| Rh H578 | | 2000 | |
| Rh H572 | 24 hr. | 700 | 0-125 |
| Rh H573 | | 300 | |
| Rh H574 | | 700 | |
| Rh H578 | | 200 | |

Figure 3. Particulate testing (clarity) of Poly-ICLC components and final product as described in the present application

|  | 10-25 microns | >25 microns |
|---|---|---|
| Components: |  |  |
| Poly I solution: | 29.4/ml | .9 |
| Poly C solution: | 16/ml | 1.7 |
| Poly lysine solution: | 94.8/ml | 3.4 |
| Carboxymethylcellulose solution: | 199.6/ml | 40.4 |
| Poly-ICLC (improved method) | 731/container | 110 |
| Poly-ICLC (older method) | >5,500 | >500 |

Table 4: Percent Survival of Malignant Glioma Patients on Poly-ICLC

| Survival | GBM<br>12 patients | AA<br>11 patients | AA (pf)<br>11 patients |
|---|---|---|---|
| 1 yr | 92% (50%†) | 100% | 100% |
| 2 yr | 50% | 100% (50%†) | 91% |
| 3 yr | 25% (2.2%†) | 91% | 82% |
| 4 yr | 17% | 91% | 82% |
| 5 yr | 8% | 91% | 73% |
| 8 yr | 8% | 82% | 36% |

GBM = glioblastoma, AA = anaplastic astrocytoma, pf = progression free survival,
† = Expected survival on standard treatment with radiation and chemotherapy.

Figure 5. Poly-ICLC Treatment of AIDS, Viral Load

Group I: Poly-ICLC Plus AZT

| PATIENT Number | P-24 Antigenemia (pcg/ml) | | | | | | | |
|---|---|---|---|---|---|---|---|---|
| | Base | 4 mo. | 8 mo. | 12mo. | 16 mo. | 20 m | 24 m | 30 m |
| PR-O1 | 89 | 15 | 21 | 305 | D | D | D | D |
| PR-O2 | 45 | 20 | 140 | - | D | D | D | D |
| PR-O3 | 0 | 80 | 34 | - | D | D | D | D |
| PR-O4 | 0 | - | 78 | 0 | 0 | 0 | 0 | - |
| PR-05 | 0 | - | - | - | - | - | - | - |
| PR-06 | 200 | - | 310 | D | D | D | D | D |
| PR-O7 | - | 346 | 35 | - | D | D | D | D |
| PR-O8 | - | 78 | 42 | 0 | 0 | 0 | 0 | - |
| 04-056 | 12 | 0 | 57 | - | D | D | D | D |
| PR-10 | 72 | - | - | 0 | 0 | 0 | - | - |
| PR-11 | 80 | 37 | - | 0 | 0 | 0 | - | - |
| PR-12 | 76 | 37 | - | 0 | 0 | 0 | - | - |
| PR-13 | 85 | - | 16 | 11 | 0 | D | D | D |
| PR-16 | 0 | 0 | 0 | 0 | - | - | - | - |
| PR-24 | 0 | 0 | 0 | 0 | - | - | - | - |

Group II: Poly-ICLC Alone

| PATIENT Number | P-24 Antigenemia (pcg/ml) | | | | | | | |
|---|---|---|---|---|---|---|---|---|
| | Base | 4 mo. | 8 mo. | 12mo. | 16 mo. | 20 m | 24 m | 30 m |
| PR-15 | 0 | 0 | 0 | D | D | | | |
| PR-17 | 0 | 0 | 0 | 0 | - | | | |
| PR-18 | 0 | - | 0 | 0 | - | | | |
| PR-19 | 117 | 31 | D | D | D | | | |
| PR-20 | 0 | 0 | 0 | 0 | - | | | |
| PR-21 | 0 | 0 | 0 | 0 | - | | | |
| PR-22 | 0 | 0 | 0 | 0 | - | | | |
| PR-23 | 808 | 704 | 440 | 200 | - | | | |

"-" = Not done

Figure 6. Poly-ICLC Treatment of Progressive Multiple Sclerosis

| CHRONIC-PROGRESSIVE MS | | | | | | | |
|---|---|---|---|---|---|---|---|
| SEX/ AGE | Mos. On PICLC | EDSS-E | AI-E | EDSS-L | AI-L | EDSS Change | Change Per yr. |
| F/29 | 128 | 7 | 8 | 8.5 | 9 | 1.5 | 0.1 |
| F/35 | 82 | 8.5 | 9 | 10 | 9 | 1.5 | 0.2 |
| M/25 | 27 | 7 | 8 | 10 | 9 | 3 | 1.3 |
| M/42 | 189 | 5 | 5 | 7.5 | 6 | 2.5 | 0.2 |
| F/39 | 136 | 8 | 9 | 9 | 9 | 1 | 0.1 |
| M/28 | 12 | 6 | 5 | 5.5 | 3 | -0.5 | -0.5 |
| M/22 | 45 | 7.5 | 7 | 8.5 | 9 | 1 | 0.3 |
| F/61 | 121 | 6.5 | 5 | 8 | 5 | 1.5 | 0.1 |
| M/49 | 164 | 6 | 4 | 6.5 | 6 | 0.5 | 0.0 |
| F/39 | 114 | 8 | 8 | 8 | 8 | 0 | 0.0 |
| M/46 | 13 | 9 | 9 | 7 | 7 | -2 | -1.8 |
| M/25 | 42 | 7 | 6 | 7.5 | 8 | 0.5 | 0.1 |
| F/59 | 26 | 5.5 | 4 | 6 | 3 | 0.5 | 0.2 |
| M/41 | 25 | 8.5 | 9 | 8.5 | 9 | 0 | 0.0 |
| F/62 | 6 | 7.5 | 8 | 7.5 | 8 | 0 | 0.0 |
| M/23 | 10 | 5.5 | 3 | 4.5 | 3 | -1 | -1.2 |
| F/50 | 85 | 6.5 | 6 | 7 | 6 | 0.5 | 0.1 |
| F/41 | 60 | 6.5 | 6 | 9 | 9 | 2.5 | 0.5 |
| F/35 | 126 | 8 | 8 | 8 | 9 | 0 | 0.0 |
| MEDIAN | 60 | 7.0 | 7.0 | 8.0 | 8.0 | 0.5 | 0.09 |
| EXACERBATING PROGRESSIVE | | | | | | | |
| SEX/ AGE | Mos. On PICLC | EDSS-E | AI-E | DSS-L | AI-L | EDSS Change | Change Per yr. |
| F/36 | 4 | 9 | 9 | 3 | 2 | -6 | -18.0 |
| F/34 | 35 | 5.5 | 2 | 6 | 3 | 0.5 | 0.2 |
| F/26 | 68 | 4.5 | 0 | 5 | 2 | 0.5 | 0.1 |
| F/55 | 85 | 4 | 2 | 3.5 | 2 | -0.5 | -0.1 |
| F/35 | 84 | 3 | 2 | 3.5 | 3 | 0.5 | 0.1 |
| M/42 | 28 | 6 | 4 | 6 | 4 | 0 | 0.0 |
| F/25 | 63 | 9.5 | 9 | 4 | 2 | -5.5 | -1.0 |
| M/22 | 3 | 8.5 | 9 | 6 | 6 | -2.5 | -10.0 |
| F/14 | 57 | 8.5 | 9 | 4.5 | 2 | -4 | -0.8 |
| F/54 | 9 | 8.5 | 9 | 8.5 | 8 | 0 | 0.0 |
| F/29 | 12 | 5 | 3 | 1 | 1 | -4 | -4.0 |
| F/34 | 25 | 5.5 | 3 | 5.5 | 3 | 0 | 0.0 |
| F/17 | 83 | 9.5 | 9 | 3 | 2 | -6.5 | -0.9 |
| MEDIAN | 35 | 6.0 | 4.0 | 4.5 | 2.0 | -0.5 | -0.1 |

EDSS-E = Kurtzke Disability Status Score on Entry; EDSS-L = EDSS at Last examination; EDSS range from 1 (mild MS) to 9 (totally disabled)

AI-E = Ambulation Index on study entry; AI-L = AI at Last Examination
  AI ranges from 1 (minimal disability) to 9 (bedridden)

METHOD FOR PREPARATION OF LARGE VOLUME BATCHES OF POLY-ICLC WITH INCREASED BIOLOGICAL POTENCY; THERAPEUTIC, CLINICAL AND VETERINARY USES THEREOF

This application claims priority from U.S. Provisional Application No. 60/393,713 filed Jul. 3, 2002.

FIELD AND BACKGROUND OF THE INVENTION

1. Field of the Invention

The present invention relates in general to methods for production and administration of pharmaceutical compounds, and more particularly to, polyriboinosinic-polyribocytidylic acid stabilized with polylysine and carboxymethylcellulose (Poly-ICLC).

2. Background Information

The invention described and claimed herein comprises an improved method for producing large lots of final sterile Poly-ICLC suitable for clinical use with reduced toxicity at effective dose levels, and a method for using Poly-ICLC clinically to treat various conditions and to regulate genes.

U.S. Pat. No. 4,349,538 (Hilton B LEVY) describes the preparation and clinical use of Poly-ICLC. However, the high doses (>300 mcg/kg) described clinically by Levy were intended to induce interferon and proved to be toxic and largely ineffectual for treatment of human patients, to the extent that, after many attempts, the experimental clinical use of poly-ICLC was largely discontinued over a decade ago. Thus, over 20 years after it was first disclosed, poly-ICLC has yet to be approved by the US Food and Drug Administration for any therapeutic indication.

Polyinosinic-Polycytidylic acid stabilized with polylysine and carboxymethylcellulose (Poly-ICLC) is a synthetic complex of polyinosinic and polycytidylic acid (double-stranded RNA (dsRNA)), stabilized with polylysine and carboxymethyl cellulose that was used as an interferon inducer at high doses (up to 300 mcg/kg IV) in short-term cancer trials some years ago. This gave mixed results with moderate toxicity, and the use of Poly-ICLC was generally abandoned when recombinant interferons became available. However, lower dose (10 to 50 mcg/kg) poly-ICLC results in a broader host defense stimulation, and enhanced clinical activity with little or no toxicity. (Salazar, Levy et al. 1996)), (Ewel, Urba et al. 1992) (Levy and Bever 1988) (Levy and Salazar 1992) (Talmadge and Hartman 1985). (Maluish, Reid et al. 1985) There are at least four interrelated clinical actions of poly-ICLC, any of which (alone or in combination) might be responsible for its antitumor and antiviral activity. These are 1) its induction of interferon; 2) its broad immune enhancing effect; 3) its activation of specific enzymes, especially oligoadenylate synthetase (OAS) and the p68 protein kinase (PKR); and 4) its multidimensional gene regulatory actions.

Interferon Induction. While induction of interferon is one of the important mechanisms for the action of poly-ICLC, interferon alone does not appear to be sufficient treatment for many conditions. In addition, the levels of serum interferon induced by our doses of Poly-ICLC are relatively low and have not in the past been associated with antiviral or antitumor action when interferon is administered alone exogenously. Immune modulation: Low dose Poly-ICLC also has a direct immune enhancing action independent of IFN, including, T-cell and natural killer cell activation, dendritic cell activation, cytokine release (e.g. interferons alpha, beta, and gamma, interleukins, corticosteroids, and TNF), and a potent adjuvant effect with increased antibody response to antigen. (Levy and Bever 1988) The immunostimulatory effects of Poly-ICLC and the interferons are complex. However, preliminary laboratory results in our pilot study in brain tumor patients showed no clear relationship between tumor response and measurable serum interferon, TNF, IL2, IL6, or neopterin. (Salazar, Levy et al. 1996) The adjuvant effect of poly-ICLC has also been demonstrated in several systems. For example, administration of low doses of poly-ICLC along with swine flu vaccination in monkeys dramatically accelerates and increases HAI titres. (Stephen, Hilmas et al. 1977). The complex interactions of the dsRNAs and the interferons in this regard are still incompletely understood, yet this seemingly paradoxical dual role of poly-ICLC as an antiviral agent and immune enhancer is consistent with its function in establishing an immediate defense system against viral attack while at the same time permitting the establishment of long term immunity. Thus, in contrast to conventional antiviral agents such as cidofovir, poly-ICLC could represent an ideal adjuvant to live virus vaccines, especially those such as smallpox vaccine that carry significant morbidity related to uncontrolled vaccine virus proliferation. In contrast to vaccination, the protective effect of dsRNAs such as poly-ICLC is also expected to be much more rapid, since the antiviral state is established within hours.

"Catalytic" Action of Poly-ICLC: OAS and PKR

The third action of Poly-ICLC is a more direct antiviral and antineoplastic effect mediated by at least two interferon-inducible nuclear enzyme systems, the 2'5' oligoadenylate synthetase (OAS) and the P1/eIF2a kinase, also known as the dsRNA dependent P68 protein kinase (PKR). (Katze 1992), (Jacobs and Langland 1996) DsRNA is not a normal component of mammalian cells, but is a byproduct of many viral infections. DsRNA induces an antiviral state in cells by functioning as an obligatory cofactor for OAS, which activates ribonuclease-L, as well as for the PKR, which inhibits initiation of protein synthesis, and for an aminotransferase that is less well studied. This may help explain the demonstrated preferential decrease of tumor protein synthesis in vivo by poly-ICLC. The OAS and PKR are very sensitive to dsRNA dose and structure (Minks, West et al. 1979). For example, simple, long chain dsRNA (as in poly-ICLC) is the most potent stimulator of OAS and PKR, while mismatched or irregular dsRNA can be inhibitory. Similarly, the PKR has both high and low affinity binding sites and is inhibited by too high a dose of dsRNA. (Galabru, Katze et al. 1989) Clinically, the OAS response is also maximal at a dose of about 30 mcg/kg Poly-ICLC, and is much diminished above 100 mcg/kg (M. Kende, N. Bernton, et al., Unpublished).

The inhibition of EFC2 glioma cells in vitro by interferon beta is also significantly associated with activation of both the OAS and PKR. Others have demonstrated that expression of a functionally defective mutant of the PKR results in malignant transformation in vitro, suggesting an important role for this enzyme in suppression of tumorigenesis. (Koromilas, Roy et al. 1992) Both PKR and poly-IC are now know to regulate the p53 tumor suppressor gene, which in turn is associated with the multiple malignancy Li-Fraumeni syndrome, which includes astrocytomas, sarcomas, lung, and breast cancers.

The clinical half-life of the OAS response to IM Poly-ICLC is about 2.5 days, suggesting an optimum dose schedule of two or three times per week (M. Kende, N. Bernton, et al., Unpublished). Patients treated with Poly-ICLC showed up to a 40-fold increase in serum OAS product in response to treatment at 10 to 20 mcg/kg, and a significant association of serum OAS with tumor response (p=0.03). Mediation of antitumor action by OAS and/or PKR activation could help explain why the high doses of Poly-ICLC used in early cancer trials were relatively ineffective.

Many viruses, including but not limited to adenovirus, pox viruses (vaccinia), foot and mouth virus, influenza, hepatitis, poliovirus, herpes simplex, SV-40, reovirus, and the human immunodeficiency virus (HIV) circumvent host defenses by down regulating OAS and/or PKR, and this effect can be reversed in vitro by exogenous dsRNA. (Jacobs and Langland 1996) A block of either PKR and/or OAS-mediated interferon action might also explain the variable response to interferons seen in both microbial and neoplastic disease. Certain viruses as well as neoplasms such as malignant gliomas may use this or a similar mechanism to circumvent host defenses and cause disease. Those diseases may thus be among the prime targets for clinical Poly-ICLC therapy using the method described herein that maximizes PKR activation.

Poly-ICLC has thus been demonstrated to have significant antiviral action against a broad variety of virus families. One example is the inhibition of vaccinia virus in several models. (Levy and Lvovsky 1978), (Burgasova 1977), (Worthington and Baron 1973) (Baron, Salazar et al. 2003) Levy & Lvovsky used poly-ICLC or placebo topical ointment in rabbits and subsequently inoculated them with intradermal injections of vaccinia virus in 10 adjacent skin sites. Local treatments were repeated at 1, 2, 3, and 4 days. Animals treated with placebo ointment developed severe lesions from days 3 to 6, and three of the eight died with vaccinia encephalitis. In contrast, poly-ICLC treated animals showed no signs of systemic disease and had much smaller skin lesions, rarely progressing beyond 1-3 mm. In separate experiments, poly-ICLC was also effective when applied after the lesions became visible. Viral titers in the skin lesions were markedly decreased (by 3 logs) in the treated animals, and interferon titers were increased. However, the mean virus-neutralizing antibody titers in the serum at 10 days was increased about 10-fold in the treated animals compared to placebo controls. While the authors appeared to suggest that the beneficial effects were due to local skin action of the poly-ICLC, they also demonstrated a robust systemic (serum) interferon response to the topical administration of the drug. This suggests that the principal protective effect may actually be systemic, which is further supported by the marked decrease or possible abrogation of systemic vaccinia dissemination by the topical poly-ICLC in their experiments.

The interaction of the type I interferons and poly-ICLC with each other in protection of the host from viral or neoplastic challenges remains unclear partly because of their overlapping functions. Nevertheless, the relationship of Poly-ICLC and the interferons can be manipulated to therapeutic advantage, At moderate to high doses, poly-ICLC is a powerful inducer of interferons, which in turn can induce synthesis of enzymes systems such as the OAS, PKR and others that themselves ultimately regulate specific protein synthesis. But, as noted above, the OAS, PKR, and likely others also require low-dose dsRNAs as obligatory cofactors to function, particularly if they have been blocked by viral and or neoplastic invasion. Low dose poly-ICLC is particularly effective clinically in this regard when administered in the regimen described in item 6 under 'Summary of the Invention' below.

Clinical Gene Regulation is a fourth mechanism by which Poly-ICLC can modify the biologic response and provide therapeutic benefit.

Plain, unstabilized poly-IC has been shown to up-regulate or down-regulate a broad variety of over 270 genes in cell culture (Geiss, Jin et al. 2001). However plain poly-IC is not effective in vivo in primates and many other species, and is of limited clinical utility. On the other hand, Poly-ICLC is expected to have broad gene regulatory actions when administered clinically in humans. These genes include but are not limited to the helicase, interferon induced protein (p56), tumor necrosis factor, interferon regulatory factor, matrix metalloproteinase, plasminogen activator, tumor protein p53, fibroblast growth factor, eukaryotic initiation factor 2, actin filament-associated protein, and VCAM-1. Some of these genes play critical roles in the body's natural defenses against a variety of neoplasms and microbial infections, and in controlling other cell functions, including protein synthesis, atherogenesis, programmed (apoptotic) cell death, cell metabolism, cellular growth, the cytoskeleton and the extracellular matrix. Gene activation is transient, lasting 24-48 hours, suggesting that repeated dosing at 2-3 day intervals will be necessary to achieve a therapeutic effect in some conditions. This is the schedule of administration that was used successfully in treatment of malignant gliomas and is further described below. (See below). For chronic or long term degenerative conditions administration may need to be extended for a period of years.

Prevention and Treatment of Ionizing Radiation Injury

Another action of dsRNAs and poly-ICLC in particular is its demonstrated protection from radiation injury. (Baze, Lvovsky et al. 1979), (Lvovsky, Levine et al. 1982) In one set of experiments, mice were treated with poly-ICLC intramuscularly at doses of 0.1 to 3 mg/kg before receiving an LD50 (30d) of ionizing radiation. Animals received either single or multiple treatments with PICLC at 8-72 hours prior to radiation exposure. Treated animals had a significantly increased survival, with a maximum dose reduction factor of 1.25. Thirty-day survival was increased by as much as 60% at a dose of about 700 Rads (From 33 to 93%). The time of maximum radioprotection did not coincide with induction of interferon, which occurred 24-48 hours earlier. This suggests that induction of enzymes such as the PKR and OAS may be more important to the radioprotective effect than simple induction of interferon. As noted above, the maximum OAS response after PICLC is about 48-72 hours after treatment with IM Poly-ICLC and coincides with the time of maximum radioprotection. Thus, a dosing schedule that maximizes not only OAS and PKR induction, but also their subsequent activation would promise an even greater radioprotective effect.

Data will be presented demonstrating the radioprotective effect of Poly-ICLC when given according to the double-dosing regimen described below that maximizes OAS and PKR activation.

Manufacture of Poly-ICLC

U.S. Pat. No. 4,349,538 (Hilton B LEVY) describes the preparation of 1-liter batches of poly-ICLC of specific composition yielding biologically active product.

However, in the preparation of large production batches (>30 liters) of poly-ICLC in accordance with good manufacturing practice (GMP), we encountered difficulties with the formulation of poly-ICLC that required critical modifications from the process described by Levy in order to yield large lots of final sterile product suitable for clinical use. Testing results indicate that those modifications resulted in a significantly improved and more biologically potent product than that described in U.S. Pat. No. 4,349,538.

SUMMARY OF THE INVENTION

The foregoing problems are overcome, and other advantages are provided by a method for producing large lots of final sterile Poly-ICLC suitable for clinical use with reduced toxicity at effective dose levels, and method for using Poly-ICLC to treat certain neoplastic, infectious and autoimmune conditions and to regulate a large variety of genes.

An improved, modified method for the production-scale manufacture of large, clinical grade, sterile batches of Poly-ICLC, a complex of high molecular weight polyriboinosinic-polyribocytidylic acid, relatively low molecular weight poly-l-lysine; and carboxymethylcellulose provides improved clarity and uniformity of composition. This improvement in the final product is expected to result in greater accuracy of drug delivery in clinical applications, with increased interferon induction and overall biological potency in primates.

In accordance with the improved method, poly-L-lysine component solution is added very slowly to the carboxymethylcellulose component solution over a period of at least 4 days. A vigorous mixing action using a large blade mixer sufficient to generate a vortex is also required for the entire blending time to minimize precipitate buildup. Proportionally stronger mixing will be required for larger amounts of preparation over 30 liters. In a preferred embodiment the carboxymethylcellulose component solution viscosity is decreased by warming to about 35° C., but not more than 40° C. in order to allow a good vortex while mixing. In a more preferred embodiment, evaporation due to warming is offset by addition of sterile water for injection during the mixing process and the polyinosinic acid component solution is clarified by warming to about 35° C. prior to sterilization by filtration.

In accordance with a second aspect of the invention, an improved, non-toxic method for utilizing Poly-ICLC in humans clinically intranasally, topically, orally, sublingually, intravenously and/or intramuscularly to modulate the expression of a broad range of genes. Similar effects have been demonstrated for plain, unstabilized poly-IC in cell culture (Geiss, Jin et al. 2001), although plain poly-IC is not effective in primates and many other species. These genes include but are not limited to the helicase, interferon induced protein (p56), tumor necrosis factor, interferon regulatory factor, matrix metalloproteinase, plasminogen activator, tumor protein p53, fibroblast growth factor, eukaryotic initiation factor 2, actin filament-associated protein, and VCAM-1. Some of these genes play critical roles in the body's natural defenses against a variety of neoplasms and microbial infections, and in controlling other cell functions, including protein synthesis, atherogenesis, programmed (apoptotic) cell death, cell metabolism, cellular growth, the cytoskeleton and the extracellular matrix. Poly-ICLC will therefore be of clinical utility in diseases in which expression of one or more of these genes is abnormal. Further, applications include similar regulation of genes in various animal species, including primates, carnivores, ungulates, poultry, and other birds.

In accordance with a third aspect of the invention, an improved method of administration (intranasally, orally, sublingually, intramuscularly, intravenously or topically) comprises administration in at least two doses spaced 4-72 hours apart, where the first dose is in a moderate range (30 to 100 mcg/kg in humans) sufficient to induce measurable but not excessive levels of serum interferon and maximal levels of PKR and OAS; and the second, lower dose is in the maximally effective range (10 to 40 mcg/kg in humans) for unblocking and stimulation of certain interferon and dsRNA inducible enzyme systems, including the PKR and 2'5'OAS, which reach their serum peaks some 48 hours post initial Poly-ICLC dosing. This approach may be extended to the use of other stabilized dsRNAs to achieve the same results. The dosing cycle may be repeated at weekly or twice weekly intervals for a varying number of cycles depending on the chronicity of the disease being treated, and may be continued for a prolonged period of time (months to several years). Finally, one or more of the dosages may be delivered utilizing a dermal patch or transdermal vehicle. (See section II under Preferred Embodiments)

In accordance with a fourth aspect of the invention, Poly-ICLC is administered clinically as above to treat certain neoplastic diseases in humans. These include but are not limited to malignant brain tumors, melanoma, breast and lung cancer, colon cancer, sarcomas, renal cell cancer, and certain leukemias and lymphomas. (See below)

In accordance with a fifth aspect of the invention, an improved, non-toxic method for utilizing Poly-ICLC clinically as above to prevent and treat microbial infections in humans by a number of viruses. These include but are not limited to arboviruses and flaviviruses such as yellow fever, West Nile virus, Japanese encephalitis and dengue (Stephen, Samos et al. 1977) (Harrington, Hlmas et al. 1977), filoviruses such as ebola, influenza, poxviruses such as smallpox and monkeypox, adenovirus, hepatitis, coronaviruses such as the SARS virus, herpesviruses such as cytomegalovirus and herpes simplex, and the human immunodeficiency virus (HIV) Certain of these viruses survive in the body by down-regulating some of the systems cited above. Further, applications include similar treatment of various animal species, including primates, carnivores, ungulates, poultry, and other birds, and include (but are not limited to) arboviruses infections such as equine encephalitis, foot & mouth virus, influenza, arteriviruses such as the Porcine PRRS virus, and bovine respiratory complex.

Further applications of the same basic invention include improved, non-toxic method for utilizing Poly-ICLC clinically as above to prevent and treat certain microbial bacterial and parasitic infections, including malaria and leishmaniasis.

Various immune disorders can also be treated with this method, including, but not limited to multiple sclerosis, Guillain Barre syndrome, immune neuropathies, and certain dys-immune vasculitides; and ionizing radiation injury.

In accordance with a sixth aspect of the invention, an improved, non-toxic method for utilizing Poly-ICLC clinically in humans as above to enhance the action and decrease the toxicity of various vaccines, including live virus vaccines.

It is therefore an object of the invention to provide an improved method of production of large lots of Poly-ICLC, suitable for clinical use.

It is a further object of the invention to provide an improved method for administration of Poly-ICLC that results in markedly decreased toxicity, and marked enhancement of its clinical and veterinary uses and its multidimensional biological effects.

It is a further object of the invention to provide a method of using Poly-ICLC to provide gene-regulatory actions in humans.

BRIEF DESCRIPTION OF THE DRAWINGS

FIG. 1 is a table showing Systemic Response to a Single Intranasal dose of Poly-ICLC in Rhesus Monkeys FIG. 2 is a table showing induction of Interferon in Rhesus Monkeys by 2 mg/kg IV of Poly-ICLC manufactured as described in the present application (lot # RBP 10036) (Compare to table I in Levy'82, U.S. Pat. No. 4,349,538, In spite of a higher dose of 3 mg/kg, the Levy preparation induced lower levels of interferon in Rhesus monkeys.)

FIG. 3 is a table showing Particulate testing (clarity) of Poly-ICLC components and final product as described in the present application FIG. 4 is a table of unpublished survival data in malignant glioma patients treated with long term, low dose Poly-ICLC.

FIG. 5 is a table showing decrease or stabilization of HIV viral load after treatment of advanced AIDS patients with low dose, long term Poly-ICLC.

FIG. 6 is an unpublished table showing low dose, long term IM Poly-ICLC Treatment of Progressive Multiple Sclerosis, showing relative stabilization, and or improvement of neurological status.

To the extent that it may aid in the understanding of the method, U.S. Pat. No. 4,349,538 (Levy) is incorporated herein by reference.

DESCRIPTION OF THE PREFERRED EMBODIMENTS

The invention is a novel method for producing large lots of final sterile Poly-ICLC suitable for clinical use with reduced toxicity at effective dose levels, and method for using Poly-ICLC to regulate genes and treat certain disease conditions.

I. Description of an Improved Method for Preparation of Large Volume Batches of Poly-ICLC with Increased Biological Potency This section is based on observations of Oncovir, in production of lot # RBP 100-36; JN: 042401RBP.

U.S. Pat. No. 4,349,538 (Levy) provides a basic description of the manufacturing process. The following modifications are disclosed. The most sensitive section of the formulation is the blending of the poly-L-lysine solution with the carboxymethylcellulose (CMC) solution. As poly-L-lysine comes into contact with CMC, a precipitate is generated which is very difficult to get back into solution. In order to prevent this precipitate the poly-L-lysine must be added very slowly to the CMC solution over a period of at least 4 days. A vigorous mixing action using a large blade mixer is also required for the entire blending time to minimize precipitate buildup.

The CMC is viscous and needs to be warmed to about 35° C., but not more than 40° C. in order to allow a good vortex while mixing. The negative impact of having heat added to the poly-L-lysine and CMC solutions is that evaporation occurs during the heating/blending/mixing process. As the solution evaporates, it becomes thicker and more difficult to mix. It is preferred to off-set some of the evaporation in the middle of the blending time to maximize the vortex action.

Evaporated solution is replaced with Sterile Water For Injection (SWFI) several times depending on the duration of mixing time. For example, a total of 15,153 ml of sterile water were added to one batch of 18L of Poly-ICLC suspension on three occasions. A stronger yet shorter blending/heating/mixing time would help minimize the quantity of water needed for evaporation replacement. No additional precipitate is generated from the addition of SWFI.

It is difficult to determine the specific gravity of the CMC solution and the final Poly ICLC solution. Neither can be done using a micro-pipetter due to viscosity. The CMC specific gravity was determined by weighting the entire bulk in a container; a line is then drawn on the container to mark the top of the solution and the CMC is removed. The container is cleaned and filled with water and weighed to determine the weight of the CMC solution vs. the weight of water. The final Poly ICLC specific gravity was determined by averaging the specific gravity of each the Poly I, Poly L, Poly C, and the CMC solutions. Poly C and Poly L each go into solution relatively well as described in Levy, '82, U.S. Pat. No. 4,349,538

The specific gravity for each can be measured using a micropipette. However, after mixing of Poly I, the solution remains hazy and clogs the filters. An important modification required was an initial heating of Poly I to clarify the solution and allow it to pass through a 0.2 micron filter with minimal loss of functional component. After heating the solution to about 35° C., it then becomes clear and can at that point be filtered for sterilization. Sterile filtration of a clear solution is also presumed to decrease any loss of active component by the filtration process. Once the Poly I is clear, it remains clear and can be re-filtered at room temperature. Sterilization for clinical use is thus accomplished with minor modifications from Levy '82 as follows: Poly I solution is filtered utilizing a 0.2 micron filter after heating to 35° C. and clarification. Poly C solution is filtered utilizing a 0.2-micron filter; Poly L solution is filtered utilizing a 0.2-micron filter. CMC solution is autoclaved.

The four solutions are then combined under sterile conditions as described above and in U.S. Pat. No. 4,349,538.

The final product produced by this method showed most of the characteristics of Poly-ICLC described in U.S. Pat. No. 4,349,538 except that it is an even more potent interferon inducer in primates. The Poly-ICLC produced with the above described modifications has a Tm of about 90° C. and is resistant to hydrolysis by pancreatic RNAase. When administered intravenously to rhesus monkeys at a dose of 2 mg/kg, it results in induction of 2,000 to 7,000 IU of interferon, with a mean of 5,750 IU of interferon eight hours post injection, as shown in table 2. This is three times higher than the values previously reported by Levy in U.S. Pat. No. 4,349,538. The new method described also results in a final product with a significantly improved clarity and uniformity of composition as demonstrated in part by particulate testing, as shown in FIG. 3.

The improved final product allows greater accuracy of drug delivery in clinical applications and greater biological potency, which may relate in part to its improved solubilization.

II. Phased Multi-Dose Treatment

The complex interaction of the interferons and dsRNA-activated systems can be manipulated to therapeutic advantage, particularly in the case of those certain microbial and neoplastic diseases that thrive by circumventing host defense mechanisms involving OAS and the PKR. One approach described by Marcus and colleagues in avian cell culture uses the combination of exogenous interferon followed by dsRNA in that order to achieve an up to 100-fold increased level of protection against avian reovirus and Newcastle disease virus over that provided by either agent alone or when given in the reverse order (Marcus and Sekellick 2001). A similar rationale can be used to treat certain human and veterinary infectious and neoplastic diseases utilizing Poly-ICLC alone. In this context, Poly-ICLC is serving two functions; first the induction of interferon, OAS, PKR, and certain other enzymes, and second the activation of the previously induce OAS, PKR, and other enzymes.

The approach described here is to first stimulate interferon induction with a moderate to high dose of Poly-ICLC, allow 4-72 hours for interferon induction of OAS, PKR and other enzyme systems, and then activate them with a second, lower dose of Poly-ICLC. Given the 2-3 day half-life of the OAS, this cycle may need to be repeated at least once or twice a week for a variable period of time depending on the disease in question. In some infections, such as mouse influenza, a single two-dose cycle of intranasal Poly-ICLC (1 mg/kg) has been shown to protect from lethal viral challenge for as long as two weeks, although the authors did not specifically pursue the high dose-low dose sequence disclosed here. (Wong, Saravolac et al. 1995) A single dose cycle was less effective.

Likewise, in the treatment of malignant gliomas, we found that less than twice weekly Poly-ICLC dosing appeared ineffectual. (Salazar, Levy et al. 1996) In that successful clinical trial (further described in the example below), dosing was spaced at 48 hours. Thus the second dose of Poly-ICLC was given at a time when the OAS (and presumably PKR) had reached peak blood levels from the first dose and could be most effectively activated by the Poly-ICLC.

Clinical trials of poly-ICLC to date have utilized the intravenous (IV) or intramuscular (IM) routes of administration. Wong and others have demonstrated that intranasal Poly-ICLC can protect from nasal viral challenge in mice. We have now have demonstrated that intranasal treatment of non-human primates (rhesus monkeys) with Poly-ICLC will also result in a robust systemic response as measured by plasma interferon at 24 hours, but not 8 hours from administration, and as shown in FIG. 1. This unexpected result opens the possibility of using intranasal, sublingual, or topical Poly-ICLC for treatment of systemic diseases. This may be especially advantageous in long term treatment of cancer or autoimmune diseases, treatment of large number of individuals exposed to a bioterror threat such as smallpox; or for veterinary use, as in containment of an outbreak of foot and mouth disease in cattle, management of the bovine respiratory complex, avian influenza, or the porcine reproductive-respiratory syndrome (PRRS)

Similarly, based on the experience with oral interferon use, it is also hypothesized that orally or sublingually administered Poly-ICLC may be sufficient to yield a clinical therapeutic response. Oral administration could also be especially advantageous in large-scale human or veterinary uses. Finally, older rabbit studies demonstrated protection from vaccinia by topically administered Poly-ICLC. This suggests that topical administration of Poly-ICLC in a dermatologic preparation or dermal patch may also be efficacious for certain applications in humans. (Levy and Lvovsky 1978) Further data will be presented to address these claims.

III. EXAMPLES

An Improved Method for the Clinical and Veterinary Use of Poly-ICLC

It is expected that Poly-ICLC, especially as improved as described above, would have application to the treatment of a variety of diseases including certain neoplastic, infectious, and autoimmune disorders.

The following examples are illustrations, but not limitations, of the approach. Given these examples, one of ordinary skill in the art could apply the same approach to other diseases.

A) Example of Clinical Gene Modulation by Poly-ICLC in Primates, Including Man

Eight Rhesus monkeys were treated intranasally with 4 ml of intranasal Poly-ICLC 2 mg/ml, followed in 24 hours with a second dose of 2 ml. Nasal secretions and cells as well as blood was collected at several intervals and specimens, including secretions, nasal epithelial cells, plasma and white blood cells were preserved for analysis. Results, including RNA microarray analysis and interferon assays will be presented.

In parallel experiments, blood will be collected from patients participating in a large multicenter clinical trial of Poly-ICLC for patients with malignant gliomas. White cell RNA will be extracted and subjected to microarray analysis to demonstrate gene activation by Poly-ICLC, including but not limited to the following genes: helicase, and interferon induced protein (p56), tumor necrosis factor, interferon regulatory factor, matrix metalloproteinase, plasminogen activator, tumor protein p53, fibroblast growth factor, eukaryotic initiation factor 2, actin filament-associated protein, and VCAM-1

These studies will not only demonstrate the spectrum of gene activation in humans by low dose Poly-ICLC, but will also reveal possible correlations to tumor response. Nevertheless, the potential clinical therapeutic uses of the ability to regulate such a broad variety of genes extends beyond the infection and neoplasm treatments described below.

B) Example of Clinical Cancer Treatment

Treatment of Malignant Gliomas

Poly-ICLC (10 to 50 mcg/kg intramuscularly one to three times weekly) was given for up to 56 months to 38 patients with glioblastoma multiforme or anaplastic astrocytoma. (Salazar, Levy et al. 1996) There was relatively low or no toxicity. Twenty of 30 patients (66%) receiving at least twice weekly Poly-ICLC (including all anaplastic astrocytoma patients) showed regression or stabilization of enhancing tumor on MRI (median=65% volume decrease). Only two of the 11 anaplastic astrocytoma patients subsequently showed tumor recurrence while on Poly-ICLC, and most of the group remain alive, with a median progression-free follow-up of over 6.5 years from diagnosis (range 22-134+months). Median overall survival is now 111+months (range 34-134+). Median Kaplan-Meir survival for glioblastoma patients on at least twice weekly Poly-ICLC treatments was 19 months; only one remains alive (98 months from diagnosis). Tumor response was associated with 2'5' oligoadenylate synthetase activation (p=0.03), but not with serum interferon, interleukins, or neopterin.

The 100% sustained tumor response or stable rate, and the prolonged, continuing, quality survival in anaplastic astrocytoma patients on Poly-ICLC contrasts favorably with the expected median survival of about 26 months for newly diagnosed AA patients on traditional chemotherapy. As suggested above, it is expected that even better survivals than those seen to date may be achievable utilizing a new double-dosing technique, as follows:

Poly-ICLC is administered intranasally, orally, sublingually, intramuscularly, intravenously or topically in at least two doses spaced 4-72 hours apart. Preferably, the first dose is in a moderate range sufficient to induce measurable but not excessive levels of serum interferon (30 to 100 mcg/kg in humans); and the second, lower dose is in the maximally effective range for unblocking and stimulation of certain interferon and dsRNA inducible enzyme systems, including the PKR and 2'5'OAS, which reach their serum peaks some 48 hours post initial Poly-ICLC dosing. For humans, the first dose would preferably be in the range of 30 to 100 mcg/kg and the second dose would preferably be in the range of 10 to 40 mcg/kg. Preferably, the doses would be spaced approximately 48 hours apart.

(See Updated, Unpublished Survival Data in Table in FIG. 4)

It is expected that this could be confirmed or suitably modified by those skilled in the art, based on the outcome of ongoing phase II clinical trials of Poly-ICLC for patients with malignant brain tumors.

A number of cancers share various characteristics with malignant gliomas, and likely utilize similar mechanisms to avoid host defenses. Such cancers may thus also be amenable to Poly-ICLC treatment using the regimen described herein. They include melanoma, and certain leukemias and lymphomas, which share abnormalities on chromosome 9p; renal cell carcinoma; and sarcomas, lung, breast, and colon cancers that occur together with gliomas in the familial Li-Fraumeni syndrome.

C) Example of Clinical Treatment of a Retroviral Disease

Treatment of AIDS with Poly-ICLC. In an open pilot trial, low dose (0.2-2 mg) PICLC was administered intramuscularly (IM) 1-3 times per week with or without Zidovudine over up to 30 months to 22 patients with HIV infection or AIDS. (Salazar, Morales et al. 1990) PICLC was well tolerated, with no significant clinical or laboratory toxicity. Side effects consisted of a mild 12-24 hour flu-like syndrome with low-grade fever and malaise at the higher doses, but usually disappeared after the first half-dozen treatments. $^{12}/_{20}$ patients showed at times dramatic initial rises in T-4 cell counts along with symptomatic improvement, although this was not uniformly maintained. Plasma P-24 titers (a measure of viral load), which were positive in $^{8}/_{16}$ patients before biweekly treatment, either became undetectable or remained so in all but one patient, whose titers were markedly elevated at onset and dropped by 75% with treatment.

In a separate dosing study of PICLC in 8 AIDS patients, neuropsychological testing has shown a marked improvement in choice reaction time and the Purdue pegboard test at 16 weeks of treatment, with a deterioration back to baseline when PICLC was discontinued. (Salazar, Martin, Levy, et al.; unpublished). This contrasts with a gradual, statistically significant deterioration in choice reaction time seen in an untreated HIV+cohort (N=41) over six months. As suggested above, it is expected that even better responses than those seen to date may be achievable utilizing the new double-dosing technique described in Section B, above, and shown in FIG. 5.

D) Example of Poly-ICLC Treatment of an Autoimmune Disorder

Treatment of Multiple Sclerosis

An open trial of high dose (100 mcg/kg) intravenous PICLC showed moderate acute toxicity in 15 patients with chronic MS; several patients improved or stabilized, but deteriorated when drug was stopped, as reported by Bever, Salazar, et al., 1986. (Bever, Salazar et al. 1986) Subsequently, Salazar continued to treat some of these and other MS patients with a completely new extended regimen using much lower doses of PICLC intramuscularly over a longer period of time. Results of this follow-up study are unpublished, and are disclosed below.

Methods: Thirty one patients with either chronic progressive (CP) or exacerbating progressive (EP) multiple sclerosis received 5-100 mcgm/kg PICLC IM q 3-14 days for up to 15 years; most received a median dose of 10 mcg/kg weekly.

Toxicity was markedly reduced to an inconstant, mild, transient malaise. The Kurtzke Expanded Disability Status Score (EDSS, which varies between 0 (normal) and 9 (totally bedridden and dependent) was used to evaluate outcome. As shown in FIG. 6, the EDSS remained stable or improved in $^{15}/_{31}$ patients (dramatically in 5). Six patients deteriorated when PICLC was stopped. The 19 CP patients showed a median EDSS change of 0.09 points per year over a median of 60 months; while the 12 EP patients showed a slight improvement (−0.1 EDSS per year) over a median of 28 months. These rates compare very favorably with the expected rates of progression in untreated multiple sclerosis patients. (Note that a lower Kurtzke score is better).

Therefore, IM low dose PICLC may be a valuable alternative to the more expensive and toxic beta-interferons for long-term management of MS. As suggested above, it is expected that even better response rates than those seen to date may be achievable utilizing the new double-dosing technique described above.

IV. A Clinical Method for Increasing the Speed and Efficacy and Decreasing the Toxicity of Vaccines, Including Live Virus Vaccines For Example, Smallpox Vaccine The strategy presented here is designed to simultaneously control vaccine side effects by decreasing viral proliferation while at the same time targeting the relevant antigens for an immune response to vaccination. It does so by stimulating the host's natural immediate response mechanisms to viral infection, including local dendritic cell activation at the time of vaccination through IM or topical administration of Poly-ICLC at the time of vaccination.

REFERENCES

Baron, S., A. Salazar, et al. (2003). *Smallpox model: Protection by IFN and Poly-ICLC despite easive mechanisms*. International Conference on Antiviral Research, Savannah, Ga.

Baze, W., E. Lvovsky, et al. (1979). "Evaluation of a nuclease resistant derivative of polyl polyC (Poly-ICLC) as a radioprotective agent." *Radiation Research* 77: 276-284.

Bever, C., A. Salazar, et al. (1986). "Preliminary trial of poly-ICLC in chronic progressive multiple sclerosis." *Neurology* 36(4): 489-493.

Burgasova, M. (1977). "Study of the antiviral activity of a poly I: Poly-C complex with poly-l-lysine in monkeys." *Antibiotiki* 22(5): 458-60.

Ewel, C., W. Urba, et al. (1992). "Polyinosinic-Polycytidylic acid complexed with poly-L lysine and corboxymethylcellulose in combination with interleukin 2 in patients with cancer: clinical and immunological effects." *Cancer Research* 52: 3005-3010.

Galabru, J., M. Katze, et al. (1989). "The binding of dsRNA and adenovirus VAI RNA to the interferon-induced protein kinase." *European Journal of Biochemistry* 178: 581-89.

Geiss, G., G. Jin, et al. (2001). "A comprehensive view of regulatio of gene expression by double-stranded RNA-mediated cell signaling." *J Biol Chem* 276(32): 30178-30182.

Harrington, D., D. Hlmas, et al. (1977). "Intranasal infection of monkeys with Japanese encephalitis virus: clinical response and treatment with a nuclease-resistant derivative of poly(I) poly(C)." *Am. J Tropical Med Hygiene* 26(6): 1191-97.

Jacobs, B. and J. Langland (1996). "When two strands are better than one: the mediators and modulators of the cellular responses to double stranded RNA." *Virology* 219: 339-349.

Katze, M. G. (1992). "The war against the interferon-induced dsRNA-activated protein kinase, can viruses win?" *Journal of Interferon Research* 12: 241-248.

Koromilas, A., S. Roy, et al. (1992). "Malignant transformation by a mutant of the IFN-inducible dsRNA dependent protein kinase." *Science* 257: 1685-1689.

Levy, H. and C. Bever (1988). Immune modulating effects of PICLC in mice, monkeys, and man. *Applied Bioactive Polymers*. C. Carraher and V. Foster. New York, Plenum.

Levy, H. and E. Lvovsky (1978). "Topical treatment of vaccinia virus infecton with an interferon inducer in rabbits." *J Infect Dis* 137(1): 78-81.

Levy, H. and A. Salazar (1992). Interferon inducers. *Interferon: Principles and Medical Applications*. S. Baron, D. Copenhaver, F. Dianzani et al. Galveston, U. Texas Medical Branch, Galveston: 65-76.

Lvovsky, E., P. Levine, et al. (1982). "Stimulation of hematopoietic stem cells by interferon inducer in non-human primates receiving fractionated total body irradiation." *Int J Radiat Oncol Biol Phys* 8(10): 1721-1726.

Maluish, A., J. Reid, et al. (1985). "Immunomodulatory effect of Poly-ICLC in cancer patients." *J Biol Resp Modif* 4: 656-663.

Marcus, P. and M. Sekellick (2001). "Combined sequential treatment with interferon and dsRNA abrogates virus resistance to interferon action." *J. Interferon Cytokine Res* 21: 423-429.

Salazar, A., H. Levy, et al. (1996). "Long-term IM Poly-ICLC treatment of malignant glioma: an open pilot study." *Neurosurgery* 38(6): 1096-1104.

Salazar, A., J. Morales, et al. (1990). "Intramuscular Poly-ICLC in HIV Infection: Preliminary findings." *Neurology* 40(Suppl 1): 238.

Stephen, E., D. Hilnas, et al. (1977). "Swine influenza virus vaccine: potentiation of antibody responses in rhesus monkeys." *Science* 197: 1289-1290.

Stephen, E., M. Samos, et al. (1977). "Effect of a nuclease resistant derivative of polyriboinosinic-polyribocytidylic acid complex on yellow fever in rhesus monkeys." *J Infect Dis* 136(1): 122-6.

Talmadge, J. and D. Hartman (1985). "Optimization of an immunotherapeutic protocol with Poly-ICLC." *Journal of Biological Response Modifiers* 4: 484-489.

Wong, J., E. Saravolac, et al. (1995). "Prophylactic and therapeutic efficacies of poly(ICLC) against respiratory influenza A virus infection in mice." *Antimicrob Agents Chemother* 39(11): 2574-2576.

Worthington, M. and S. Baron (1973). "Effect of poly IC and antibody on infection of immunosuppressed mice with vaccinia virus." *J Infect Dis* 128(3): 308-11.

While illustrated with respect a to method for producing large lots of final sterile Poly-ICLC suitable for clinical use with reduced toxicity at effective dose levels, and method for using Poly-ICLC to regulate genes, and manage certain disease conditions, the invention may be applied to any method for producing large lots of final sterile Poly-ICLC suitable for clinical use with reduced toxicity at effective dose levels, and method for using Poly-ICLC to regulate genes using the same techniques, modified to adapt to method for producing large lots of final sterile Poly-ICLC suitable for clinical use with reduced toxicity at effective dose levels, and method for using Poly-ICLC to regulate certain genes in a manner which would be known to one skilled in the art.

What is claimed is:

1. An improved, modified method for the production-scale manufacture of clinical grade, sterile batches of poly-ICLC, a complex of high molecular weight polyriboinosinic-polyribocytidylic acid; poly-L-lysine; and carboxymethylcellulose, having biological potency and interferon induction activity in primates, comprising the steps of adding poly-L-lysine component solution very slowly to a carboxymethylcellulose component solution over a period of at least 4 days, and mixing for the entire blending time vigorously enough to form a vortex and minimize precipitate buildup.

2. The method of claim 1, wherein the viscosity of the carboxymethylcellulose is decreased by warming to about 35 degree C., but nor more than 40 degree C. so as to allow a vortex while mixing.

3. The method of claim 1, wherein evaporation due to warming is offset by addition of sterile water for injection during the mixing process.

4. The method of claim 1 further comprising the addition of a polyriboinosinic acid component solution which is clarified by warming to about 35 degree C. prior to sterilization by filtration.

* * * * *